United States Patent [19]
Kilbourn et al.

[11] Patent Number: 5,312,835
[45] Date of Patent: * May 17, 1994

[54] USE OF CARDIOTONIC DRUGS AND INHIBITORS OF NITRIC OXIDE SYNTHESIS TO ALLEVIATE PATHOLOGIC HYPOTENSION

[75] Inventors: Robert G. Kilbourn, Houston, Tex.; Steven S. Gross, New York, N.Y.; Owen W. Griffith, Milwaukee, Wis.

[73] Assignees: Board of Regents, the University of Texas System, Austin, Tex.; Cornell Research Foundation, Inc., Ithaca, N.Y.

[*] Notice: The portion of the term of this patent subsequent to Jul. 2, 2008 has been disclaimed.

[21] Appl. No.: 890,430

[22] Filed: May 29, 1992

Related U.S. Application Data

[63] Continuation-in-part of Ser. No. 838,814, Mar. 13, 1992, which is a continuation-in-part of Ser. No. 406,909, Sep. 13, 1989, Pat. No. 5,028,627.

[51] Int. Cl.⁵ .................. A61K 31/195; A61K 31/135
[52] U.S. Cl. .................................... 514/565; 514/648; 514/930
[58] Field of Search .......................... 514/565, 648, 930

[56] References Cited

U.S. PATENT DOCUMENTS

| | | | |
|---|---|---|---|
| 4,282,217 | 8/1981 | Baglioni et al. | 424/240 |
| 5,028,627 | 7/1991 | Kilbourn et al. | 514/565 |
| 5,059,712 | 10/1991 | Griffith | 562/560 |

FOREIGN PATENT DOCUMENTS

| | | |
|---|---|---|
| WO91/04024 | 9/1990 | PCT Int'l Appl. |
| PCT/US90/05199 | 2/1991 | PCT Int'l Appl. |
| WO91/84023 | 4/1991 | PCT Int'l Appl. |

OTHER PUBLICATIONS

*Merck Manual*, pp. 404–411, 1982 (especially p. 409).
*Remington Pharmaceutical Sciences*, p. 882, 1982.
Gardiner et al Chem Abst 114(7):59571 (1990).
International Search Report (dated Oct. 29, 1993) PCT04940.
Komas et al., "Endothelium dependent and independent relaxation of rat aorta by cyclic nucleotide phosphodiesterase inhibitors", *Br. J. Pharmacol.*, 104(2):495–503, see Medline Abstract 92182837 (Oct. 1991).
Moncada et al., "Nitric Oxide: Physiology, Pathophysiology, and Pharmacology," *Pharmacological Reviews*, 43(2):109–142, 1991, published in USA.
Moncada et al., "The L-Arginine: Nitric Oxide Pathway," *Journal of Cardiovascular Pharmacology*, 17(Suppl. 3):S1–S9, 1991, published in USA.
Parratt, J. R., and Stoclet, Jean-Claude, "Possible Role of Nitric Oxide in Refractory Hypotension Associated with Sepsis and Endotoxaemia and with Multiple Organ Failure," *Applied Cardiopulmonary Pathophysiology*, 4:143–149, 1991, published in USA.
Johnston, Jeff, "Molecular Science Sets Its Sights On Septic Shock," *The Journal of NIH Research*, 3:61–65, 1991, published in USA.

(List continued on next page.)

*Primary Examiner*—Frederick E. Waddell
*Assistant Examiner*—Gregory Hook
*Attorney, Agent, or Firm*—Arnold, White & Durkee

[57] ABSTRACT

The present invention involves a method for prophylaxis or treatment of an animal for systemic hypotension induced by endotoxin and/or a biological response modifier such as the cytokines, IFN, TNF, IL-1 or IL-2 and the like. Said method involves administering, preferably intravascularly, a therapeutically effective amount of dobutamine and an inhibitor of nitric oxide formation from arginine. Although preferable administration is intravascular, it is contemplated that other parenteral administration routes such as intraperitoneal, intramuscular or subdermal injection, for example, may prove useful. Enteral or topical administration of arginine analogs may also prove beneficial under certain clinical conditions.

4 Claims, 3 Drawing Sheets

OTHER PUBLICATIONS

Moncada, S., and Higgs, E. A., "Endogenous Nitric Oxide: Physiology, Pathology and Clinical Relevance," *European Journal of Clinical Investigation*, 21:361–374, 1991, published in Europe.

Palmer et al., "Nitric Oxide Release Accounts for the Biological Activity of Endothelium-Derived Relaxing Factor," *Nature*, 327:524–526, 1987, published in the United Kingdom.

Martin et al., "Selective Blockade of Endothelium-Dependent and Glyceryl Trinitrate-Induced Relaxation by Hemoglobin and by Methylene Blue in the Rabbit Aorta," *The Journal of Pharmacology and Experimental Therapeutics*, 232(3):708–716, 1985, published in USA.

Buga et al., "Endothelium-Derived Nitric Oxide Relaxes Nonvascular Smooth Muscle," *European Journal of Pharmacology*, 161:61–72, 1989, published in Europe.

Torti et al., "A Macrophage Factor Inhibits Adipocyte Gene Expression: An in Vitro Model of Cachexia," *Science*, 229:867–871, 1985, published in USA.

Vallance et al., "Effects of Endothelium-Derived Nitric Oxide on Peripheral Arteriolar Tone in Man," *The Lancet, Ltd.*, 997–999, Oct., 1989, published in Europe.

Old, Loyd J., "Tumor Necrosis Factor (TNF)," *Science*, 23:630–632, 1985, published in USA.

Yoshida and Kasama, "Biotransformation of Nitric Oxide," *Environmental Health Perspectives*, 78:201–206, 1987, published in USA.

Reif and Simmons, "Nitric Oxide Mediates Iron Release from Ferritin," *Archives of Biochemistry and Biophysics*, 283(2):537–541, 1990, published in USA.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics*, 241(1):307–313, 1987, published in USA.

Kosaka et al., "The Interaction Between Nitrogen Oxides and Hemoglobin and Endothelium-Derived Relaxing Factor," *Free Radical Biology and Medicine*, 7:6-53–658, 1989, published in USA.

Chevion et al., "Iron-Nitrosyl Bond configuration in Nitrosyl-Hemoproteins: A Comparative EPR Study of Hemoglobin A and Hemoglobin Kansas," *Israel Journal of Chemistry*, 15:311–317, 1976, published in Israel.

Collier and Vallance, "Second Messenger Role for NO Widens to Nervous and Immune Systems," *Trends in Pharmacological Sciences Including Toxicological Sciences*, Elseview Science Publishers, Ltd., front page and pp. 428–431, 1989, published in United Kingdom.

Ignarro et al., "Endothelium-Derived Relaxing Factor Produced and Released from Artery and Vein is Nitric Oxide," *Proc. Natl. Acad. Sci. USA*, 84:9265–9269, 1987, published in USA.

Murray et al., "Stabilization and Partial Characterization of Endothelium-Derived Relaxing Factor from Cultured Bovine Aortic Endothelial Cells," *Biochemical and Biophysical Research Communications*, 141(2):689–696, 1986, published in USA.

Marletta, Michael A., "Nitric Oxide: Biosynthesis and Biological Significance," name of publication unknown, Elseview Science Publishers, Ltd., pp 448–493, 1989, published in United Kingdom.

Sakuma, I. et al., (1988) "Identification of Arginine as a Precursor of Endothelium-Derived Relaxing Factor," *Proc. Natl. Acad. Sci. USA*, 85:8664–8667, published in U.S.A.

Abstract entitled "Nitric Oxide Damages DNA in Bacteria," *Chem. and Engineering News*, Nov. 18, 1991, published in U.S.A.

Wink et al., (1991) "DNA Deaminating Ability and Genotoxicity of Nitric Oxide and its Progenitors," *Science*, 254:1001–1003, published in U.S.A.

Kilbourn et al., (1984), "Activated Macrophages Secrete a Soluble Factor that Inhibits Mitochondrial Respiration of Tumor Cells," *J. Immunology*, 133:2577–2581, published in U.S.A.

Kilbourn et al., (1990) "Reversal of Endotoxin-Mediated Shock by $N^G$-Methyl-L-Arginine, an Inhibitor of Nitric Oxide Synthesis," *Biochem. and Biophys. Res. Commun.*, 172:1132–1138, published in U.S.A.

Kilbourn, R. G., et al., (1990) "$N^G$-Methyl-L-Arginine Inhibits Tumor Necrosis Factor-Induced Hypotension: Implications for the Involvement of Nitric Oxide," *Proc. Natl. Acad. Sci. USA*, 87:3629–3632, published in U.S.A.

Schmidt et al., (1992) "Insulin Secretion from Pancreatic B Cells Caused by L-Arginine-Derived Nitrogen Oxides," *Science*, 255:721–723, published in U.S.A.

Turan, A. et al., (1975) "Removal of the Nitro Group from Nitroarginine and Nitroarginine Peptides," *Acta Chimica Academiae Scientiarum Hungaricae*, Thomas, 85:327-published in Europe.

Iyengar, R. et al., (1987) "Macrophage Synthesis of

OTHER PUBLICATIONS

Nitrite, Nitrate, and N-Nitrosamines: Precursors and Role of the Respiratory Burst," *Proc. Natl. Acad. Sci. USA*, 84:6369-6373, published in U.S.A.

Stuehr et al., (1987) "Induction of Nitrite/Nitrate Synthesis in Murine Macrophages by BCG Infection, Lymphokines, or Interferon-$\gamma^1$ *J. Immunology*, 139:518-525, published in U.S.A.

Marletta et al., (1988) "Macrophage Oxidation of L-Arginine to Nitrite and Nitrate: Nitric Oxide Is an Intermediate," *Biochemistry*, 27:8706-8711, published in U.S.A.

Palmer, R. M. J. et al., (1988) "Vascular Endothelial Cells Synthesize Nitric Oxide from L-Arginine," *Nature*, 333:664-666, published in the United Kingdom.

Palmer, R. M. J. et al. (1988) "L-Arginine is the Physiological Precursor for the Formation of Nitric Oxide in Endothelium-Dependent Relaxation," *Biochem. Biophys. Res. Commun.*, 153:1251-1256, published in U.S.A.

Schmidt et al., (1988) "Arginine is a Physiological Precursor of Endothelium-Derived Nitric Oxide," *European J. Pharmacology*, 154:213-216, published in Europe.

Aisaka et al., (1989) "$N^G$-Methylarginine, An Inhibitor of Endothelium-Derived Nitric Oxide Synthesis, Is a Potent Pressor Agent in the Guinea Pig: Does Nitric Oxide Regulate Blood Pressure in Vivo?" *Biochem. Biophys. Res. Commun.*, 160:881-886, published in U.S.A.

Rees, D. D. et al., (1989) "Role of Endothelium-Derived Nitric Oxide in the Regulation of Blood Pressure," *Proc. Natl. Acad. Sci. USA*, 86:3375-3378, published in U.S.A.

Stuehr, D. J., et al., (1989) "Activated Murine Macrophages Secrete a Metabolite of Arginine with the Bioactivity of Endothelium-Derived Relaxing Factor and the Chemical Reactivity of Nitric Oxide," *J. Exp. Med.*, 169:1011-1020, published in U.S.A.

Stuehr, D. J. et al., (1989) "Synthesis of Nitrogen Oxides from L-Arginine by Macrophage Cytosol: Requirement for Inducible and Constitutive Components," *Biochem. Biophys. Res. Commun.*, 161:420-426, published in U.S.A.

Piguet et al., (1989) "Tumor Necrosis Factor/Cachectin Plays a Key Role in Bleomycin-Induced Pneumopathy and Fibrosis," *J. Exp. Med., 170:655-663, published in U.S.A.*

Kilbourn et al., (1990) "Endothelial Cell Production of Nitrogen Oxides in Response to Interferon $\gamma$ in Combination with Tumor Necrosis Factor, Interleukin-1, or Endotoxin," *J. Natl. Cancer Instituted*, 82:772-776, published in U.S.A.

Gross et al. (1991) "Cytokine-Activated Endothelial Cells Express an Isotype of Nitric Oxide Synthase Which Is Tetrahydrobiopterin-Dependent, Calmodulin-Independent and Inhibited by Arginine Analogs with a Rank-Order of Potency Characteristic of Activated Macrophages," *Biochem. Biophys. Res. Commun.*, 178:823-829, published in U.S.A.

Kilbourn et al., (1990) "$N^G$-Methyl-L-Arginine Inhibits Tumor Necrosis Factor-Induced Hypotension: Implications for the Involvement of Nitric Oxide," *Proc. Natl. Acad. Sci. U.S.A.*, 87:3629-3632, published in U.S.A.

Gennaro, Alfonso R., Editor, and Chairman of the Editorial Board (1990)"Sympathomimetic Drugs", *Remington's-Pharmaceutical Sciences*, 18th Edition, p. 877, published in U.S.A.

Windholz, Martha, Editor, (1983) "Dobutamine," *The Merck Index, An Encyclopedia of Chemicals, Drugs, and Biologicals*, Tenth Edition, 3407. p. 495, published in U.S.A.

Goodman and Gilman, "Catecholamines and Sympathomimetic Drugs," *The Pharmacological Basis of Therapeutics*, Eighth Edition, 189, 202-203, 214-215, published in U.S.A.

Klabunde and Ritger, (1991), "N hu G-Monomethyl-L-Arginine (NMA) Restores Arterial Blood Pressure but Reduces Cardiac Output in a Canine Model of Endotoxic Shock," *Biochemical and Biophysical Research Communications*, 178(3):1135-1140, published in U.S.A.

Klabunde, et al. (1991), "Cardiovascular Actions of Inhibitors of Endothelium-Derived Relaxing Factor (Nitric Oxide) Formation/Release in Anesthetized Dogs," *European Journal of Pharmacology*, 199:51-59, published in the Netherlands.

Vincent, et al. (1990), "Dobutamine Administration in Septic Shock: Addition to a Standard Protocol," *Critical Care Medicine*, 18(7):689-693, published in U.S.A.

Vincent et al. (1990), "Septic Shock: Particular Type of Acute Circulatory Failure," *Critical Care Medicine*, 18(1):S70-S74, published in U.S.A.

Shoemaker et al. (1990), "Therapy of Shock Based on Pathophysiology, Monitoring, and Outcome Prediction," *Critical Care Medicine*, 18(1):S19-S25, published in U.S.A.

Schremmer et al. (1990), "Heart Failure in Septic Shock: Effects of Inotropic Support," *Critical Care Medicine*, 18(1):S49-S55, published in U.S.A.

USE OF CARDIOTONIC DRUGS AND INHIBITORS OF NITRIC OXIDE SYNTHESIS TO ALLEVIATE PATHOLOGIC HYPOTENSION

This is a continuation-in-part of copending U.S. Ser. No., filed Mar. 13, 1992 which is a continuation-in-part of U.S. Ser. No. 07/406,909, filed Sep. 13, 1989 issued Jul. 2, 1991 as U.S. Pat. No. 5,028,627, both of which are incorporated by reference herein.

BACKGROUND OF THE INVENTION

The present invention relates to the alleviation of hypotension induced by nitrogen oxide production. Research relating to the present invention was supported by government research grants which gives the United States government rights in the present invention.

In 1980, Furchgott and Zawadski (*Nature* 288:373-376 1980) demonstrated that endothelial cells, which line blood vessels, can be stimulated to release a substance which relaxes vascular smooth muscle i.e., causes vasodilatation. Since the chemical nature of this substance was completely unknown, it was simply named endothelium-derived relaxing factor (EDRF). It is now widely accepted that many naturally-occurring substances which act as physiological vasodilators mediate all or part of their action by stimulating release of EDRF; these substances include acetylcholine, histamine, bradykinin, leukotrienes, ADP, ATF, substance P, serotonin, thrombin and others. Although the extremely short lifetime of EDRF (several seconds) hampered efforts to chemically identify this molecule, in 1987 several laboratories suggested that EDRF may be nitric oxide (NO.), which spontaneously decomposes to nitrate and nitrite. A fundamental problem in accepting this No. hypothesis was that mammalian systems were not known to contain an enzymatic pathway which could synthesize NO.; additionally, a likely precursor for NO. biosynthesis was unknown. After observing that the arginine analog $N^G$-methyl-L-arginine (L-NMA) could inhibit vascular EDRF/NO. synthesis induced by acetylcholine and histamine, and that EDRF/NO. synthesis could be restored by adding excess L-arginine, it was proposed that arginine is the physiological precursor of EDRF/NO. biosynthesis (Sakuma et al., *PNAS* 85:8664-8667, 1988). Additional evidence supporting this proposal was reported almost simultaneously. It was also later demonstrated that inhibition of EDRF/NO. synthesis in the anesthetized guinea pig raises blood pressure, suggesting that EDRF/NO. is an important physiological regulator of blood pressure (Aisaka et al., *BBRC* 160:881-886, 1989). Notwithstanding the accumulated evidence supporting synthesis of NO., it is understood by those skilled in the art that other nitrogen oxides may be present and may be active in reducing blood pressure. Within this specification, the acronym NO. will be understood to represent nitric oxide and any additional vasoactive nitrogen oxides.

It was demonstrated that macrophage cells become "activated" by 12-36 hour treatment with gamma-interferon, bacterial endotoxin and various cytokines. This "activation" is associated with initiation of tumor cell killing and generation of nitrite and nitrate from L-arginine. It was also observed that activated macrophages actually make NO. from L-arginine (just like endothelial cells) and that this NO. subsequently reacts with oxygen to form more oxidized nitrogen metabolites which appear to be physiologically inert (Stuehr et al., *J. Exp. Med.* 169:1011-1020, 1989). The enzyme responsible for NO. synthesis (nitric oxide synthase) has been partially characterized by some of the present inventors (Stuehr et al. *BBRC* 161:420-426, 1989) and acts to oxidize the terminal amino group of arginine, resulting in production of NO. and citrulline. It is now believed that macrophage-derived NO. is an important tumoricidal and bactericidal agent. Since bacterial endotoxin, gamma-interferon and other cytokines can trigger NO. generation by macrophage cells it appeared that: 1) endothelial cell NO. generation may be stimulated by similar stimuli and 2) septic shock (i.e., systemic vasodilatation induced by bacterial endotoxin) may result from massive activation of NO. biosynthesis. Speculation that the latter hypothesis was correct was fueled by a prior report that urinary nitrate levels are grossly elevated by treatment of rats with bacterial endotoxin (Wagner et al., *PNAS* 80:4518-4521, 1983).

Cytokines are well known to cause morphological and functional alterations in endothelial cells described as "endothelial cell activation". Distinct immune-mediators such as tumor necrosis factor (TNF), interleukin-1 (IL-1), and gamma-interferon (IFN or I) appear to induce different but partially overlapping patterns of endothelial cell activation including increased procoagulant activity (Bevilaqui et al., *PNAS* 83:4533-4537, 1986), PGI2 production (Rossi, *Science* 229,174, 1985), HLA antigen expression (Pober et al., *J. Immunol.* 138:3319-3324, 1987) and lymphocyte adhesion molecules (Cavender et al., *J. Immunol.* 138:2149-2154, 1987). Although these cytokines are reported to cause hypotension, vascular hemorrhage, and ischemia, the underlying mechanisms of altered vasoactivity are unclear (Goldblum et al., *Infect. Immun.* 57:1218-1226, 1989; Tracey et al., *Science* 234:470, 1986). A potential mediator of altered vasoactivity is EDRF.

In both clinical and animal (Dvorak, et al., *J. Nat'l. Canc. Inst.* 81:497-502, 1959) studies on the effects of biological response modifiers a major dose limiting toxicity has been hypotension and vascular leakage.

The cardiotonic drug dobutamine has been used as an addition to a standard treatment protocol, to treat patients in septic shock. Results obtained indicated that dobutamine did not significantly increase mean arterial pressure but did increase oxygen supply and consumption (Vincent et al., 1980, *Critical Care Medicine* 18:689-693).

Kilbourn et al. described a decrease in blood pressure and cardiac output in dogs treated with endotoxin or IL-1 (*BBRC* 178:823-829, 1991; *JNCI* 1992 in press). The administration of $N^G$-methyl-L-arginine (NMA) partially restored blood pressure but further decreased cardiac output. This result was recently confirmed by Klabunde et al. (Klabunde *BBRC* 178:1135-1140, 1991). Further studies showed that NMA decreases cardiac output in normal animals (not treated with endotoxin) an effect which is increased at higher doses of NMA (Kilbourn et al. *BBRC* 178:823-829, 1991; Klabunde et al. *Eur. J. Pharm.* 199:51-59, 1991).

SUMMARY OF THE INVENTION

The present invention involves a method for prophylaxis or treatment of an animal for systemic hypotension induced by endotoxin and/or a biological response modifier such as the cytokines, IFN, TNF, IL-1 or IL-2 and the like. Said method involves administering, preferably intravascularly, a therapeutically effective amount of dobutamine and an inhibitor of nitric oxide formation from arginine. Although preferable administration is intravascular, it is contemplated that other parenteral administration routes such as intraperitoneal, intramuscular or subdermal injection, for example, may prove useful. Enteral or topical administration of nitric oxide formation inhibitors such as arginine analogs may also prove beneficial under certain clinical conditions.

In one embodiment the preferred NO. formation inhibitor is $N^G$-substituted-arginine or $N^G,N^G$-disubstituted arginine which is administered to an animal possibly developing or experiencing NO.-induced systemic hypotension. The arginine analogs of the present invention are preferably of the L configuration and include any pharmaceutically acceptable addition salts as commensurate with planned treatments.

A particular use of the method of the present invention is for prophylaxis or treatment of systemic hypotension induced in a patient by chemotherapeutic treatment with tumor necrosis factor, interleukin-2 or both. In this aspect, the method involves intravascularly administering to the chemotherapy patient a therapeutically effective amount of a cardiotonic drug such as dobutamine and an arginine analog such as an $N^G$-substituted arginine or an $N^G,N^G$-disubstituted arginine.

An important aspect of the present invention is as a method for treatment of an animal for systemic hypotension induced by endotoxin, i.e., septic shock. Although prophylaxis is less practical here, treatment is essential. The treatment involves intravascularly administering to such a hypotensive animal a therapeutically effective amount of cardiotonic drug and an inhibitor of NO. formation such as an arginine analog. Preferred arginine analogs include $N^G$-methyl-L-arginine, $N^G$-amino-L-arginine or $N^G$-nitro-L-arginine, and the like.

Septic shock is a life-threatening condition that results from exposure to bacterial endotoxin. It is manifested by cardiovascular collapse and mediated by the release of cytokines such as tumor necrosis factor. Some of these cytokines cause the release of vasoactive substances. In the present study, administration of bacterial endotoxin to dogs caused a decrease in peripheral vascular resistance and a fall in mean arterial blood pressure. Vascular resistance and systemic arterial pressure were normalized after administration of a cardiotonic drug such as dobutamine and $N^G$-methyl-L-arginine, a potent and selective inhibitor of nitric oxide synthesis. These findings indicate that nitric oxide overproduction is an important contributor to endotoxic shock. Moreover, these findings demonstrate for the first time, the utility of dobutamine in combination with nitric oxide synthesis inhibitors in the treatment of endotoxic shock.

$N^G$-substituted arginine analogs of the L configuration for uses as described herein include $N^G$-amino-L-arginine, $N^G$-nitro-L-arginine, $N^G$-ethyl-L-arginine, $N^G$-propyl-L-arginine or $N^G$-butyl-L-arginine and the like. Other arginine analogs of this or related types which inhibit NO. synthesis are also usable. Therapeutically effective amounts of the substituted or disubstituted arginine analogs inhibit production in the animal or patient of nitric oxide from arginine, thus obviating its hypotensive effects.

Treatment with the NO. production inhibitor is accompanied by treatment of a hypotensive patient with a therapeutically effective amount of an inotropic drug dobutamine, for example, or other such cardiotonic drug. Dobutamine, a preferred cardiotonic drug, is normally a racemic mixture having little effect on peripheral vascular resistance. The $\alpha_1$ receptor mediated vasoconstriction of the (−) dobutamine isomer is apparently counterbalanced by the $\alpha_1$ receptor antagonist activity of the (+) dobutamine isomer. Both isomers are $\beta$ receptor agonists, the (+) isomer being more effective, thus relating to the inotropic and chronotropic effects. Although dobutamine is the preferred cardiotonic or inotropic drug to be used in conjunction with the arginine analog NO. production inhibitors, it is understood that other cardiotonic drugs such as amrinone, milrinone and cardiac glycosides, for example, may also be used to alleviate any cardiosuppressive effects of arginine analogs and/or contribute to vasoconstrictive effects.

In a more general sense, the present invention relates to a method for prophylaxis or treatment of an animal or systemic hypotension induced by undesired production of nitric oxide. Said method involves intravascularly administering to an animal a therapeutically effective amount of a cardiotonic drug such as dobutamine as well as an agent such as an arginine analog inhibiting production of nitric oxide from arginine. Effective arginine analogs include a wide variety of compounds, particularly derivatives of arginine and the like which inhibit nitric oxide production. Other inhibitory agents may have substituents, for example, on the guanidino group of arginine or analogous ornithine and citrulline functional groups and should serve as well.

Synthesis of hypotension-producing nitric oxide may be directly or indirectly induced by at least one of IFN, TNF, IL-1, IL-2 and endotoxin. In a preferred aspect, the arginine analogs usable as described herein include $N^G$-substituted arginine or $N^G,N^G$-disubstituted arginine. In one embodiment, these analogs preferably have alkyl substituents selected from the group consisting of methyl, ethyl, propyl and butyl. Analogs may include derivatized alkyl substituents selected from the group consisting of hydroxyalkyl, carboxyalkyl and aminoalkyl. The arginine analogs usable in the practice of the present invention also include arginine with at least one $N^G$ substituent selected from the group consisting of alkyl, hydroxyalkyl, and alkenyl. The therapeutically effective amount of arginine analogs of the present invention is an amount sufficient to inhibit production of nitric oxide from arginine so that, in combination with an inotropic drug such a dobutamine, undesired hypotension is reversed and lowered cardiac output is avoided. Nitric oxide rapidly degrades to nitrite and nitrate ions in the presence of oxygen; since nitrites are oxidized in vivo to nitrate, nitrates may be measured clinically to indicate nitric oxide production.

When intravascularly administering to a dog a therapeutically effective amount of the preferred $N^G$-methyl-L-arginine (NMA) the therapeutically effective amount is between about 1 mg/kg and about 100 mg/kg. The appropriate dose for a human of NMA and/or other arginine antagonists should be between about 0.1 mg/kg and about 100 mg/kg.

Dobutamine, the preferred cardiotonic drug, having a relatively short circulation life, should be intravascularly infused at doses between about 2.5 $\mu$g/kg/min and about 20 $\mu$g/kg/min.

DESCRIPTION OF THE PREFERRED EMBODIMENTS

Effective treatment of pathogenic hypotension, for example that caused by endotoxin in septic shock, is an object of the present invention. The treatment comprises concomitant administration of a cardiotonic drug and an inhibitor of nitric oxide production. The preferred cardiotonic drug is dobutamine and the preferred inhibitor is $N^G$-methyl-L-arginine. These agents, when administered together cause a surprising synergistic blood pressure elevation.

Septic shock is a life-threatening condition that results from exposure to bacterial endotoxin and is manifested by cardiovascular collapse. Response to endotoxin is mediated by the release of cytokines such as tumor necrosis factor and interleukin-1 which cause the induction of an isoform of nitric oxide synthase that produces pathological amounts of nitric oxide (NO.). In vitro experiments with cytokine-treated endothelial cells show that, once induced, NO. production may persist even after removal of the inducing stimulus. The present inventors have demonstrated that inhibitors of NO. biosynthesis, such as NMA, can rapidly reverse the hypotension in dogs treated with TNF, IL-1 or endotoxin. The anti-hypotensive effects are augmented by simultaneous administration of dobutamine, an inotropic agent. Since the highest mortality from septic shock occurs in the first 24–48 hours, inhibition of the final vasoactive mediator of endotoxic shock has theoretical advantages over approaches utilizing IL-1 receptor antagonists or antibodies against endotoxin and/or TNF.

The experiments below describe use of $N^G$-methyl-L-arginine, an anti-hypotensive agent, with dobutamine (Dobutrex, Eli Lilly), an agent which stimulates heart contractions, to increase blood pressure. The invention and discovery is a new method of use for dobutamine since by itself dobutamine has little effect on blood pressure. However, combined with NMA the two agents act synergistically to increase blood pressure. The mechanism of this marked vasopressor effect of the combination of these two agents is incompletely understood. This is an improvement over either agent alone in that $N^G$-methyl-L-arginine reverses low blood pressure due to sepsis or cytokine-induced hypotension by about 50–90%, depending upon the severity of the cardiovascular collapse. The addition of dobutamine augments the anti-hypotensive effects of NMA and results in more fully effective cardiovascular function. The administration of a combination of NMA and dobutamine to normal dogs results in a massive increase in blood pressure (350/220 mm Hg) whereas neither agent alone increases blood pressure more than 10–15 mm (typically 130–140/90–100 mm Hg). This shows that there is a synergistic activity between the two drugs that is not present when either drug is used alone.

Figure 1A:
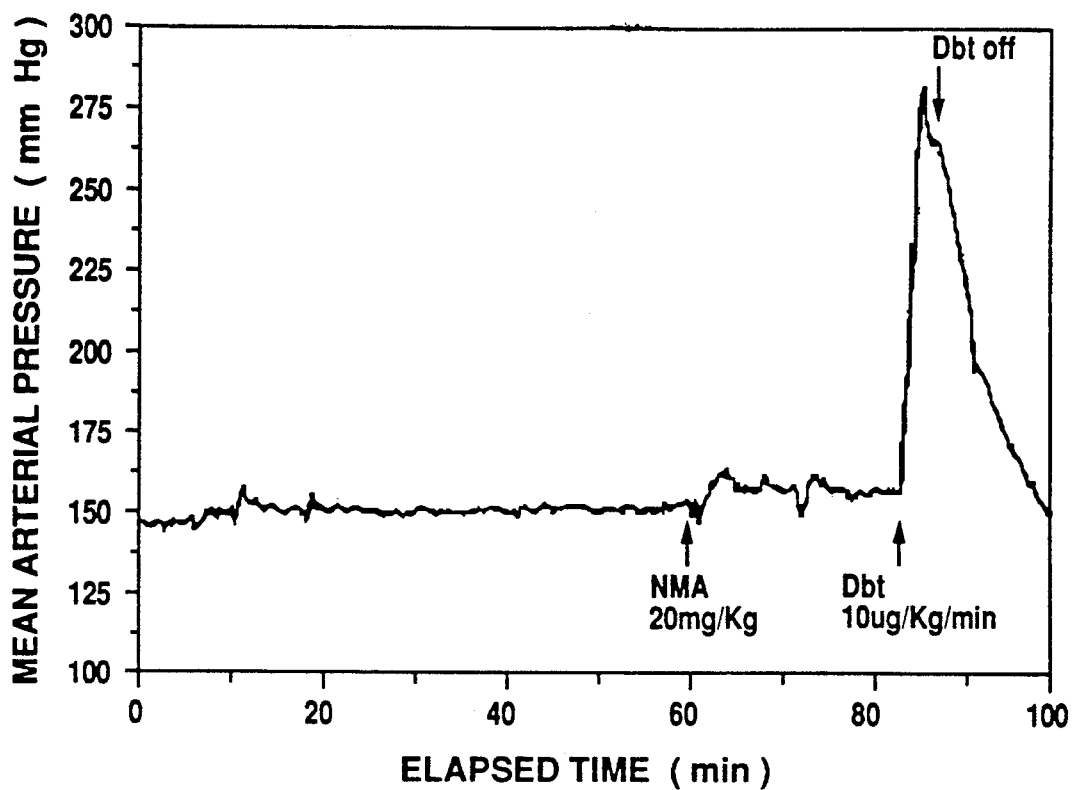
FIG. 1A shows mean arterial blood pressure of a pentobarbital anesthetized dog treated with NMA and dobutamine.

For FIG. 1A the animal was pretreated with 100 mg of indomethacin I.V. to inhibit prostacyclin synthesis. This treatment has no effect on nitric oxide production. After one hour of baseline measurements, the animal received NMA (20 mg/kg) resulting in a small increase in blood pressure. Twenty minutes later dobutamine (10 µg/kg/min) was administered resulting in a marked increase in blood pressure which was noted to return to normal after discontinuation of dobutamine.

Figure 1B:
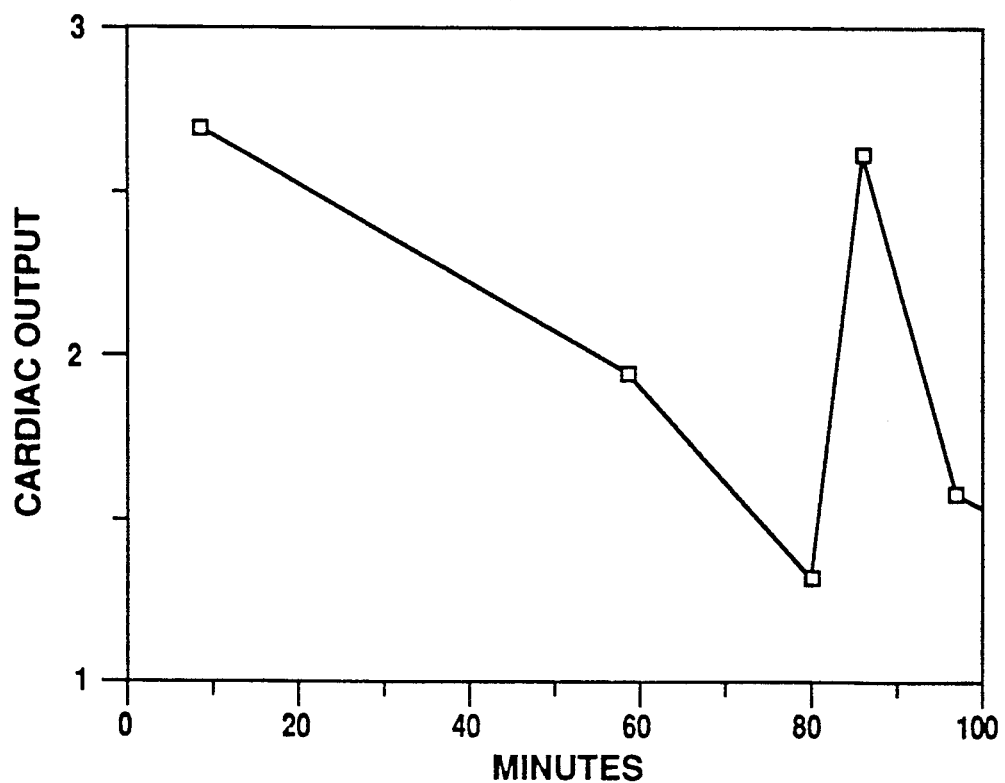
FIG. 1B shows cardiac output in an anesthetized dog treated with NMA and dobutamine.

For FIG. 1B the initial (baseline) cardiac output was 2.71 which was decreased to 1.30 after administration of NMA. This decrease in cardiac output was almost completely reversed by administration of 10 µg/kg/min of dobutamine (cardiac output=2.61). This effect was reversed by discontinuation of the dobutamine which resulted in a decrease in the cardiac output to the level observed after administration of NMA.

Figure 2:
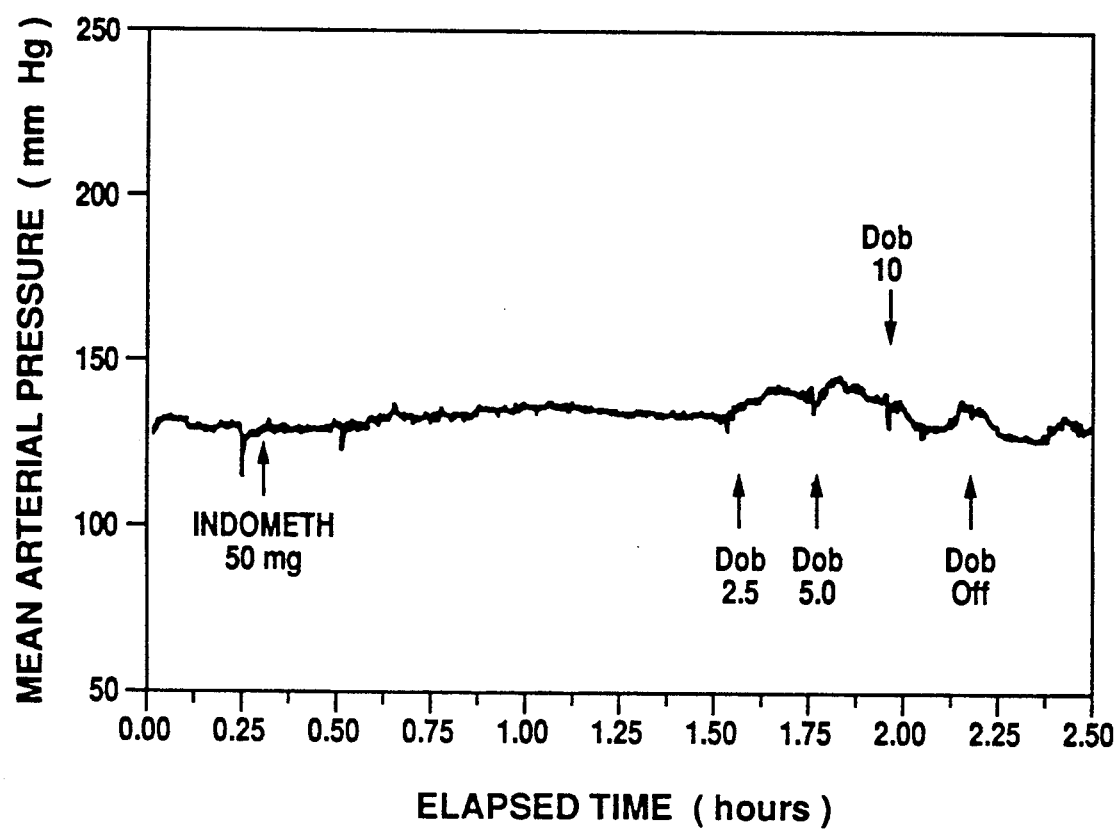
FIG. 2 shows mean arterial blood pressure of a pentobarbital anesthetized dog treated with dobutamine alone.

Certain experimental observations which support this invention are described in FIGS. 1, 2 and 3. In FIGS. 1A and 1B the blood pressure tracing of a normal dog which is anesthetized with pentobarbital and intubated for respiratory support is shown. Indomethacin was administered to the anesthetized dog at the start of each experiment to inhibit prostacyclin synthesis. Administration of dobutamine at doses up to 10 µg/kg/min did not alter mean arterial pressure (See FIG. 2). The dog received a single IV dose of 20 mg/kg NMA (NMA alone, 1st arrow) with an increase in the blood pressure of only 12 mm Hg.

The combination of NMA and dobutamine (Dobutrex) results in a marked increase in blood pressure. Administration of Dobutrex at 10 µg/kg/min combined after administration of NMA (20 mg/kg), increased the blood pressure by 121 mm Hg (2nd arrow). The infusion of Dobutrex was discontinued and blood pressure again reached baseline. Dobutamine alone had no significant effect on resting blood pressure in the absence of NMA (FIG. 2).

Figure 3A:
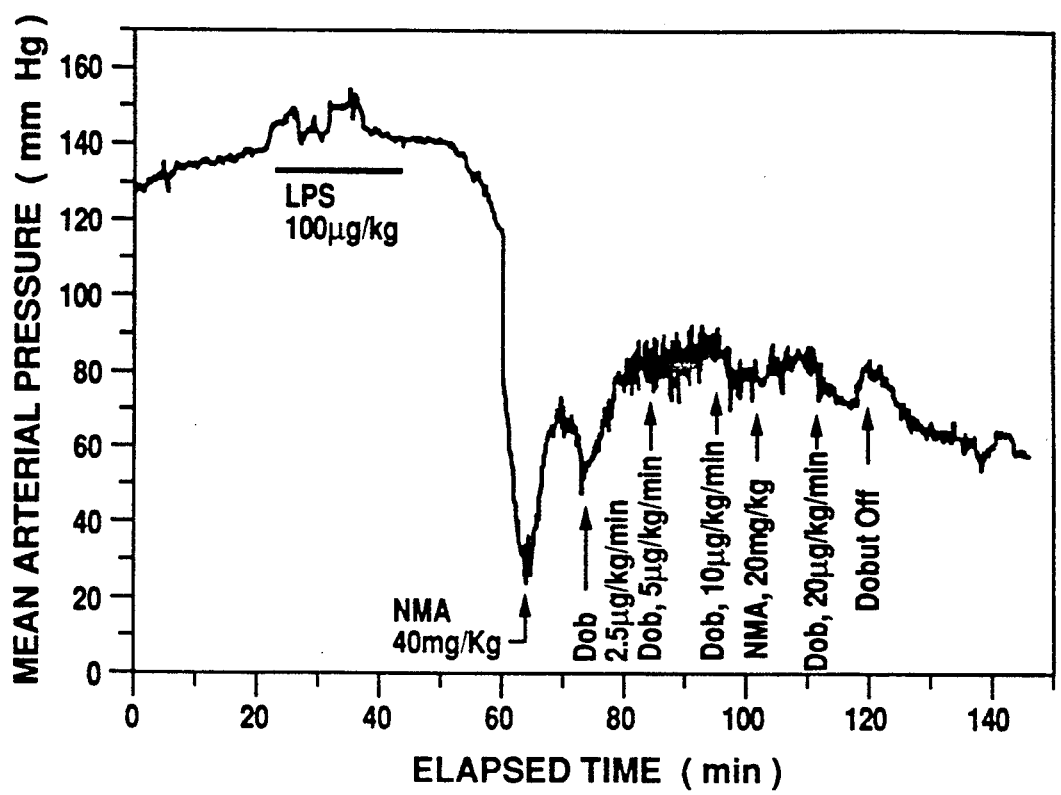
FIGS. 3A and 3B show the effect of dobutamine and NMA in endotoxemic dogs.

In a separate experiment, a dog was treated with endotoxin (LPS) (100 µg/kg) and the blood pressure was subsequently noted to decline to by 121.5 mm Hg to 23.3 mm Hg (FIG. 3A). In FIG. 3A an anesthetized dog received 100 mg of indomethacin to inhibit prostacyclin and baseline mean arterial blood pressure was measured for 20 minutes. Endotoxin (lipopolysaccharide-LPS); 100 µg/kg) was administered over a 20-minute period. Forty minutes after the start of the endotoxin infusion the blood pressure was noted to decrease. NMA was administered by I.V. bolus (40 mg/kg) resulting in a 49.3 mm Hg increase in blood pressure. The blood pressure was increased further by administration of 2.5 µg/kg/min of dobutamine to a level of 91 mm Hg (an increase of 67.7 mm Hg). Administration of NMA resulted in an increase in blood pressure ($\Delta=49.6$ mm Hg; 2nd arrow). This anti-hypotensive effect was significantly augmented by coadministration of 2.5 µg/kg/min of Dobutrex ($\Delta=67.7$ mm Hg; FIG. 3A, 2nd arrow). Further elevations of Dobutrex levels only further increased MAP to a maximum of 91 mm Hg.

Figure 3B:
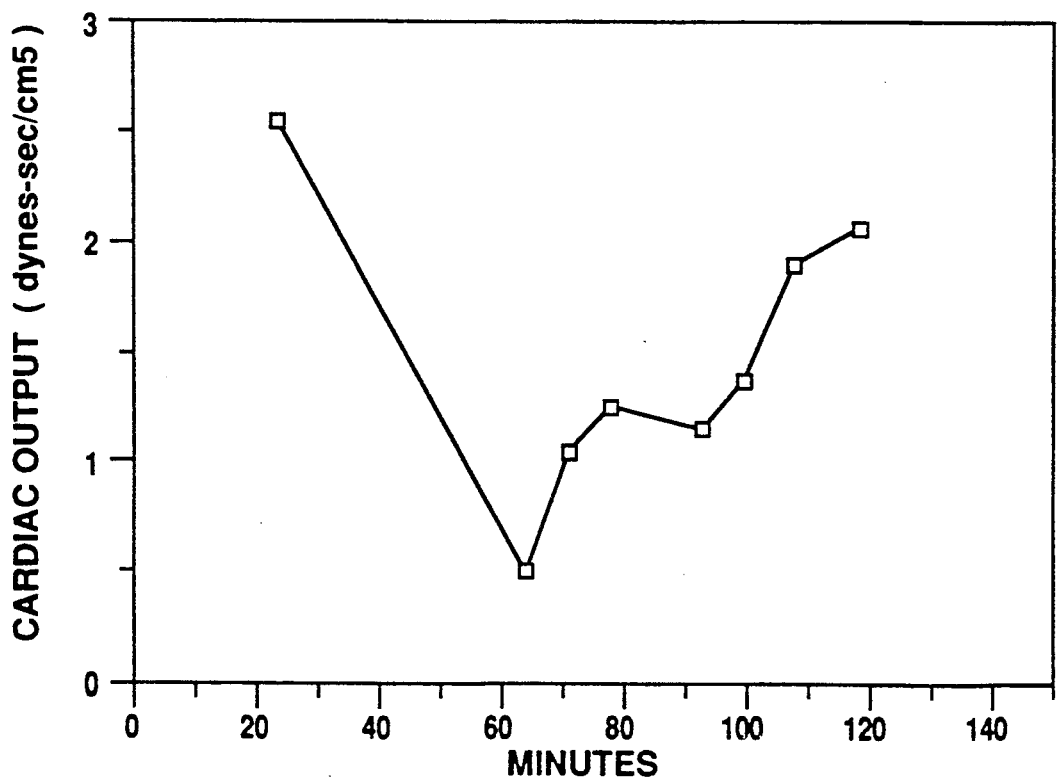

Administration of NMA alone resulted in a decline in the cardiac output (FIG. 1B). This decline in cardiac output after NMA administration was reversed by administration of dobutamine (10 µg/kg/min). In endotoxemic, hypotensive animals, a decline in cardiac output was noted prior to administration of NMA. This low cardiac output was slightly increased after administration of NMA (FIG. 3B). Administration of dobutamine further increased the cardiac output in a dose-dependent fashion with almost complete reversal of the low cardiac output with 20 μg/kg/min of dobutamine (110 minutes, FIG. 3B). In FIG. 3B cardiac output was measured prior to administration of endotoxin (LPS) and was noted to decline 40 minutes after the start of the LPS infusion. This decrease in cardiac output was reversed by dobutamine in a dose-dependent fashion such that administration of dobutamine at 20 μg/kg/min almost completely reversed the change in cardiac output due to endotoxin and NMA.

The references cited above are incorporated by reference herein for the reasons cited. It is understood that changes may be made in the particular arginine analogs, cardiotonic drugs and methods of the invention without departing from the equivalents of the following claims.

What is claimed is:

1. A method for treating hypotension induced by nitric oxide in septic shock, the method comprising concomitantly intravascularly administering a therapeutically effective amount of dobutamine and $N^G$-substituted L-arginine or $N^G$, $N^G$-disubstituted L-arginine, whereby mean arterial pressure and cardiac output are increased.

2. The method of claim 1 wherein the $N^G$-substituted L-arginine or $N^G$, $N^G$-disubstituted L-arginine is $N^G$-methyl-L-arginine.

3. A method for treating hypotension attendant to septic shock comprising concomitantly intravascularly administering $N^G$-methyl-L-arginine and dobutamine in effective therapeutic amounts to a patient in septic shock, whereby mean arterial pressure and cardiac output are increased.

4. The method of claim 1 or 3 wherein the intravascular administering of arginine analog or $N^G$-methyl-L-arginine is intravenous.

* * * * *

UNITED STATES PATENT AND TRADEMARK OFFICE
CERTIFICATE OF CORRECTION

PATENT NO. : 5,312,835
DATED : May 17, 1994
INVENTOR(S) : Kilbourn et al

It is certified that error appears in the above-indentified patent and that said Letters Patent is hereby corrected as shown below:

In claim 4, column 8, line 18, delete "arginine analog" and insert --$N^G$-substituted L-arginine, $N^G,N^G$-disubstituted L-arginine-- therefor.

Signed and Sealed this

Sixth Day of September, 1994

Attest:

BRUCE LEHMAN

*Attesting Officer*    *Commissioner of Patents and Trademarks*